United States Patent [19]
Akiyama

[11] 4,416,762
[45] Nov. 22, 1983

[54] ELECTROPHORETIC APPARATUS

[75] Inventor: Junichi Akiyama, Kyoto, Japan

[73] Assignee: Shimadzu Corporation, Kyoto, Japan

[21] Appl. No.: 360,765

[22] Filed: Mar. 22, 1982

[30] Foreign Application Priority Data

Jul. 31, 1981 [JP] Japan .............................. 56-121018
Jul. 31, 1981 [JP] Japan .............................. 56-121019

[51] Int. Cl.³ .......................................... B01D 13/02
[52] U.S. Cl. .......................... 204/299 R; 204/180 G
[58] Field of Search .......... 204/299 R, 180 G, 180 R, 204/195 R

[56] References Cited

U.S. PATENT DOCUMENTS 3,620,958 11/1971 Dijksterhuis et al. ........... 204/299 R
3,649,499 3/1972 Virtanen et al. ................. 204/180 R
3,932,264 1/1976 Haruki et al. ................... 204/299 R
3,941,678 3/1976 Akiyama ......................... 204/299 R
4,295,949 10/1981 Fujiwara et al. ................. 204/180 G

FOREIGN PATENT DOCUMENTS 2303846 8/1974 Fed. Rep. of Germany ... 204/299 R

Primary Examiner—R. L. Andrews
Assistant Examiner—Terryence F. Chapman
Attorney, Agent, or Firm—Hubbell, Cohen, Stiefel & Gross

[57] ABSTRACT

An isotachophoretic apparatus which is equipped with means for discriminating whether each of the zones of a sample having been separated by electrophoresis is a completely separate one having already been separated into a single component or an incompletely separate one. The discriminating means is constructed of means for detecting zones at different instants, e.g., two usual detectors, means for detecting the length of the zones, e.g., a time counter and means for comparing the lengths of the two corresponding zones and judging the completion of separation, e.g., a microcomputer.

8 Claims, 6 Drawing Figures

ELECTROPHORETIC APPARATUS

BACKGROUND OF THE INVENTION

1. Field of the Invention

The present invention relates to an electrophoretic apparatus of the type, in which terminal and leading electrolyte bathes are connected to both the ends of a high voltage power supply circuit, respectively, in which an electrophoretic column is connected between those electrolyte bathes and in which a sample introduction system and a measurement system are arranged in this order in the electrophoretic column.

2. Description of the Prior Art

In the prior art, there is an isotachophoretic apparatus using terminal and leading electrolytes. More specifically, there is recently proposed in U.S. Pat. Nos. 3,932,264 or 3,941,678 a capillary type isotachophoretic apparatus which uses a capillary tube as an electrophoretic column. In the apparatus thus proposed, however, it can not be judged whether or not the separation of sample components is complete thereby to allow the electrophoresis to be effected at a uselessly long distance or to invite a fear that notwithstanding that the migration distance is so insufficient that the zone is still the mixed one of the sample components it is misjudged as one of a single component.

SUMMARY OF THE INVENTION

It is, therefore, an object of the present invention to provide an isotachophoretic apparatus which is equipped with means for discriminating whether each of the zones of a sample having been separated by electrophoresis is a completely separate one having already been separated into a single component or an incompletely separate one.

The aforementioned discriminating means is constructed of means for detecting zones at different instants, means for detecting the length of the zones detected and means for comparing the lengthes of the two corresponding zones obtained thereby to judge a zone as one having a completely separated single component in case the two zones can be deemed to be equal.

The zone detecting means described in the above is, for example, two usual electrophoretic detectors which are disposed along an electrophoretic tube at a spacing from each other. On the other hand, the length detecting means described in the above is, for example, a time counter for measuring the time interval from the instant when the leading end of the zone is detected by the stationary one of the aforementioned electrophoretic detectors to the instant when the trailing end of that zone is detected. Moreover, the judging means described in the above is, for example, a microcomputer which is so programmed as to make a remainder between the two lengthes of the corresponding zones obtained by the aforementioned time counter thereby to generate an output indicating the judgement of completely separate zones in case that difference is equal to or less than a predetermined value.

The zone detecting means described in the above may desirably be constructed of, for example, a single electrophoretic detector which is to be moved along an electrophoretic tube. In this case, the length detecting means is constructed of means for detecting the moving distance of that detector.

Another object of the present invention is to provide an isotachophoretic apparatus which is further equipped with means for determining the length of a component zone on the basis of the lengthes of an incompletely separate zone detected at different instants when that incompletely separate zone is completely separated.

The aforementioned means is, for example, a microcomputer which is so programmed as to determine a rate from the change in the length of the incompletely separate zone at different instants and to determine from that rate of change the time period for which any mixed zone is wholly vanished thereby to determine the length of the completely separate component zone from that time period and the rate of change determined in advance.

A further object of the present invention is to provide an isotachophoretic apparatus which is further equipped with means for determining the quantity of a sample for an incompletely separate zone to complete the separation of its components at a predetermined electrophoretic distance on the basis of the length of the incompletely separate zone detected at different instants.

The aforementioned means is, for example, a microcomputer which is so programmed as to determine the quantity of the sample reduced to shorten the length of the incompletely separate zone at a previous instant by the zone length at a subsequent instant.

A further object of the present invention is to provide an isotachophoretic apparatus which is further equipped with means for displaying completion of separation, in case all the zones of a sample are judged as completely separate ones, and incompletion of separation in the otherwise case.

The aforementioned means is constructed of, for example, a microcomputer, which is so programmed as to calculate the difference in the lengthes of all the zones of the sample obtained at different instants thereby to generate an output indicating the completion of separation only when the differences can be wholly deemed to be zero, and a lamp which is lit by that output.

The aforementioned and other objects and advantages of the present invention will become apparent from a reading of the detailed description of the preferred embodiments taken in view of the accompanying drawings.

DESCRIPTION OF THE PREFERRED EMBODIMENTS

Figure 1:
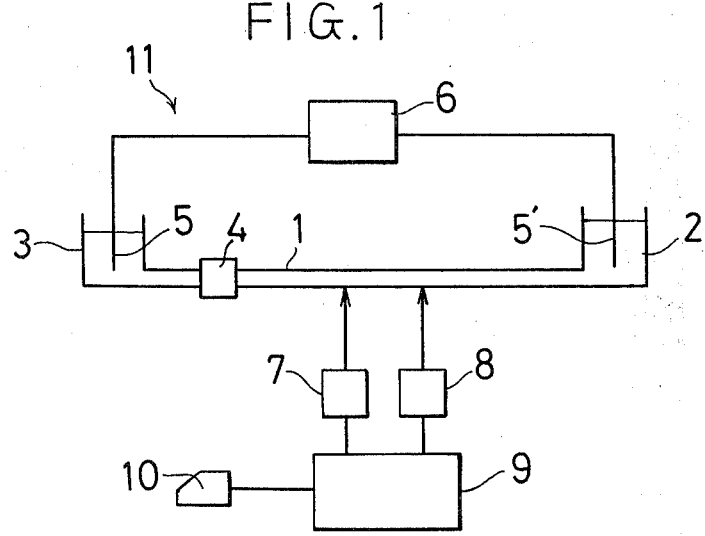
FIG. 1 is a schematic view showing a capillary type electrophoretic apparatus according to one embodiment of the present invention.

FIG. 1 shows one embodiment of the present invention. In this isotachophoretic apparatus 11, reference numeral 1 indicates a capillary tube having both its ends connected to electrolyte bathes 2 and 3, in which electrodes 5 and 5' connecting a d.c. constant current power supply 6 are inserted. Numeral 4 is a sample introducing device. Numerals 7 and 8 indicate detectors which are used in the present invention so as to measure potential gradients, respectively, and which may be any of the usual electrophoretic detectors. Numeral 9 indicates an operation circuit such as a microcomputer which is also used in the present invention. Numeral 10 indicates a control board.

A leading electrolyte L is introduced into the bath 2 whereas a terminal electrolyte T is introduced into the bath 3, and there is formed at the position of the sample introducing device 4 a boundary of the two electrolytes, between which a sample solution S is interposed. A constant current is fed to the electrolytes. Any of the leading electrolyte L, the terminal electrolyte T and the sample solution S contains charged particles (which will be shortly called "ions"), and the ions in the sample solution S are differentiated in accordance with their mobilities in the electric field established. The leading electrolyte L is a solution of the ions having the highest mobility whereas the terminal electrolyte T is a solution of the ions having the lowest mobility. All the various ions contained in the sample have such a mobility as is lower than that of the ions in the leading electrolyte L and higher than that of the ions in the terminal electrolyte T (In other words, the leading electrolyte L and the terminal electrolyte T are selected so.). If the electrophoresis is effected in that way, the respective component ions in the sample are separated in accordance with the levels of their mobilities so that the respective component ion zones are gradually formed and are shifted as a whole to the right of the drawing. Since the lengthes of the zones of the respective component ions thus having been formed are in proportion to both the concentrations of the respective component ions and the quantity of the sample, the quantitative analysis can be conducted by measuring the lengthes of the zones. The operation of this isotachophoresis is well known in the art.

Figure 2:
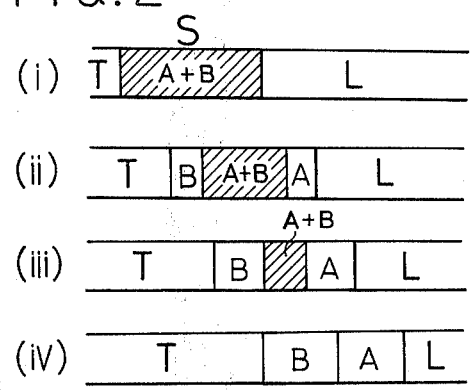
FIG. 2 is a diagram illustrating the time changes of a mixed zone.

Now, let's consider the sample S containing two kinds of ions A and B. In FIG. 2, (i) shows a zone which is generally uniformly mixed immediately before the migration. As the migration advances, that mixed zone is separated into a homogeneous zone of the ions A, a mixed zone of the ions A+B and a homogeneous zone of the ions B, as shown in FIG. 2(ii). As the migration further advances, the mixed zone of the ions A+B is shortened, as shown in FIG. 2(iii). As the migration still further advances, the mixed zone of the ions A+B is vanished to leave only the two zones A and B, as shown in FIG. 2(iv).

If the time changes of the potential gradients at respective positions are recorded by means of the potential gradient detectors 7 and 8, the potential gradient of the leading electrolyte L at first is the lowest because the ion mobility is the highest. When the zone having the sample components is reached, the potential gradient is stepwise increased so that the records shown in FIG. 3 can be obtained. The base portion at the lefthand extremity of those records expresses the potential gradient in the leading electrolyte L whereas the top at the righthand extremity expresses the potential gradient in the terminal electrolyte T. The steps A and B correspond to the zones of the sample components whereas the steps A+B correspond to the mixed zones. The records thus far described are pherograms, of which a pherogram $f_1$ is obtained by the detector 7 and a pherogram $f_2$ is obtained by the detector 8. Since the detector 7 is located upstream of the detector 8 in the migration direction, the pherogram $f_1$ indicates the separate state of the components at an earlier stage than the pherogram $f_2$. Since the potential gradients of the respective zones in the pherograms $f_1$ and $f_2$ are unchanged with the time, the corresponding relationships between the respective steps of the pherograms $f_1$ and $f_2$ obtained by the detectors 7 and 8, respectively, are found in view of the potential gradients of the respective zones.

While both of the pherograms $f_1$ and $f_2$ show three zones, they may lead to a misjudgement that the sample S contains three kinds of ions, because the completion of separation of the sample S can not be observed by a zone at any of the pherograms $f_1$ and $f_2$ without referring to the corresponding zone.

Figure 3:
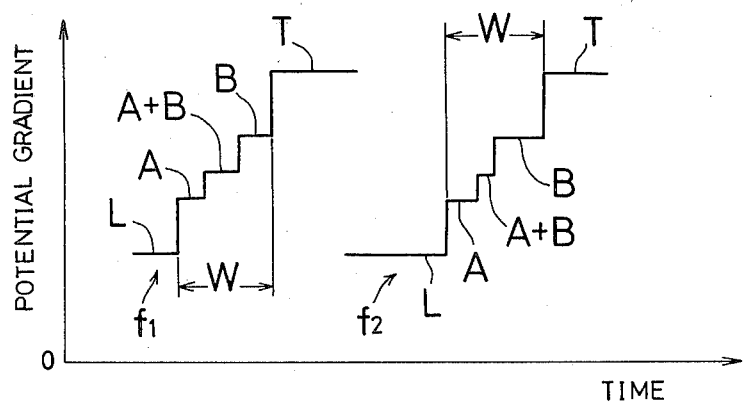
FIG. 3 is a diagram illustrating one example of the respective pherograms which are drawn on the basis of the outputs of the two detectors of the apparatus shown in FIG. 1.

As will be understood from FIGS. 2 and 3, however, the mixed zone has its length gradually decreased with the time until it is vanished. On the contrary, the zones upstream and downstream of that mixed zone have their lengthes gradually increased with the time. According to the general expression, more specifically, if a certain component zone is completely separated by the isotachophoresis, it will not broaden further. On the contrary, the incompletely separate homogeneous zones will broaden with the time whereas the mixed zone will narrow with the time. Then, the lengthes of the zones having their potential gradients corresponding to each other are compared as to the pherograms $f_1$ and $f_2$ which have been obtained by the detectors 7 and 8. If the zone lengthes compared are found to be substantially equal, it is possible to judge that the particular zone is a completely separate one. On the contrary, if the pherogram $f_2$ at the later instant is shorter, it is possible to judge the zone under consideration as a mixed one.

The apparatus 11 according to the present invention is based upon a principle that whether or not a certain zone is a homogeneous one is judged in view of the aforementioned point, and is intended to realize that principle.

The operation circuit 9 is made operative to differentiate the outputs of the detectors 7 and 8, to count the number of clock pulses within a time period from one differential pulse to a subsequent differential pulse by means of a counter thereby to detect the zone lengthes at the respective steps of FIG. 3, and to store those zone lengthes together with the potential gradients at the respective steps (i.e., zones) in a memory. In short, the zone lengthes are concretely captured in terms of time duration.

Next, the operation circuit 9 compares each step of the pherogram $f_1$ or the output of the detector 7 and the corresponding one (which is found because of the equal potential gradient) of the pherogram $f_2$ of the detector 8 thereby to locate such a zone as has a zone length difference equal to or smaller than a predetermined value. If such zone is found, it is judged as a completely separate zone because it is assumed to have a substantially equal length.

Next, both a zone having its length shortened in the pherograms $f_1$ and $f_2$ and a zone to be found in the pherogram f₁ but not in the pherogram f₂ are located. The zones thus located are mixed ones, and the latter zone is one which is prepared as a result that the mixed zone has been completely separated at the position of the detector 8 into its upstream and downstream zones.

With closer reference to FIG. 3, the zones A and B are longer by the predetermined value or more in the pherogram f₂ that in the pherogram f₁, and the zone A+B sandwiched in between is shorter in the pherogram f₂. It follows that the zone A+B is found to be a mixed one. Moreover, since the mixed zone exists in the pherogram f₂, it is also found that the separation of that sample is still incomplete.

Then, the operation circuit 9 judges that there is no completely separate zone, and feeds the control board 10 with an output indicating the incomplete separation.

Figure 4:
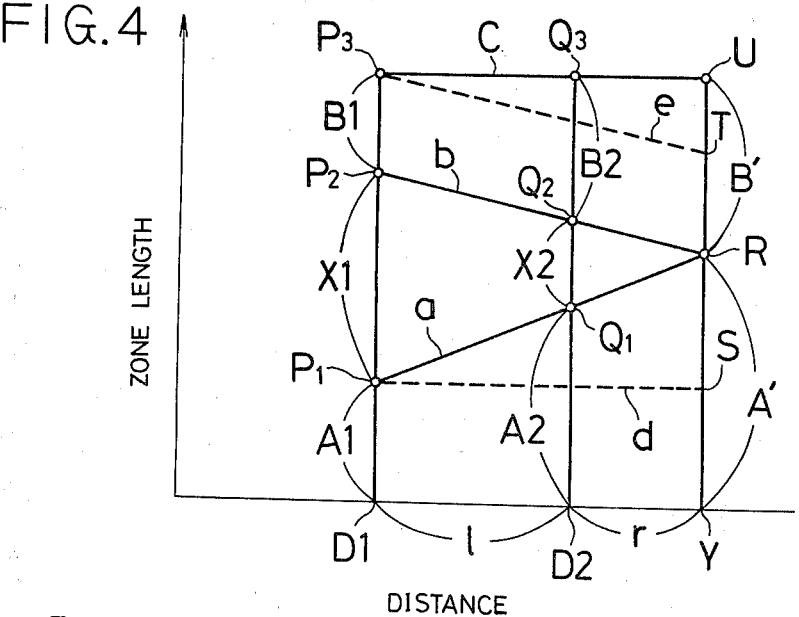
FIG. 4 is a graph illustrating the changes in the lengthes of respective zones with a migration distance.

Now, FIG. 4 is a graph in which the length of a zone is plotted against the lengthwise distance of the electrophoretic tube 1. Positions D1 and D2 located on the abscissa correspond to those of the detectors 7 and 8, respectively. At both the points D1 and D2, there are drawn vertical lines, on which the lengthes of the zones A, A+B and B are marked, and measuring lines a, b and c are drawn by joining the lengthwise ends of the respective zones. Here, the time lengthes of the zones A, A+B and B in the pherogram f₁ are indicated at A1, X1 and B1, respectively, whereas the time lengthes in the pherogram f₂ are indicated at A2, X2 and B2. The measuring lines a and b intersect at a point R. More specifically, it is found that the zone A+B is vanished, when the electrophoresis advances to the point R, and is completely separated into the zones A and B. And, the lengthes of the zones A and B at this time are indicated at A' and B'. If the point drawn on the abscissa by extending a vertical line from the point R is indicated at Y and if the distance between the points D1 and D2 is indicated at l whereas the distance between the points D2 and Y is indicated at r, the following Equation holds:

$$\frac{X1}{l+r} = \frac{X2}{r} \quad (I)$$

Moreover, an auxiliary line d is drawn from a point P₁ in parallel with the abscissa, and a triangle P₁RS is to be considered. Then, the following Equation is obtained:

$$\frac{A2 - A1}{l} = \frac{A' - A1}{l + r} \quad (II)$$

Likewise, an auxiliary line e is drawn from a point P₃ in parallel with a line P₂R, and a triangle P₃UT is to be considered. Then, the following Equation is obtained:

$$\frac{B2 - B1}{l} = \frac{B' - B1}{l + r} \quad (III)$$

those Equations (I), (II) and (III) are rearranged in the following forms:

$$r = \frac{X2}{X1 - X2} \times l \quad (I')$$

$$A' = \frac{(A2 - A1)(l + r) + l \cdot A1}{l} ; \text{ and} \quad (II')$$

$$B' = \frac{(B2 - B1)(l + r) - l \cdot B1}{l} \quad (III')$$

The operation circuit 9 is so programmed as to conduct the calculations of the aforementioned Equations (I'), (II') and (III') on the basis of the pherograms f₁ and f₂ obtained thereby to claculate the values r, A' and B', which designate the migration diatance from the detector 8 to the separation completion position and the lengthes of the respective component zones A and B after the complete separation, respectively. From these lengthes, the quantities of the respective components are determined.

Reverting to FIG. 4, the zone A+B is shortened by (X1-X2) between the point D1 and the point D2. Therefore, if the length of the zone A+B is (X1-X2) at the point D1, the separation is completed (In other words, the mixed zone is vanished.) at the point D2. Now, if the electrophoresis is conducted by means of a suitable quantity W₀ of sample so that the length of the mixed zone is X1 at the point D1, the zone length is (X1-X2) just at the point D1 if the sample is reduced such times of the quantity W₀ of the sample introduced at first as is expressed as follows:

$$\frac{X1 - X2}{X1} \quad (IV)$$

The operation circuit 9 is, therefore, so programmed as to conduct the calculation expressed in the following Equation (V):

$$W = W_o \times \frac{X1 - X2}{X1} \quad (V)$$

The quantity W calculated by the above Equation (V) is one in which the separation of the components can be completed at a predetermined migration distance to the position of the detector 8.

Figure 5:
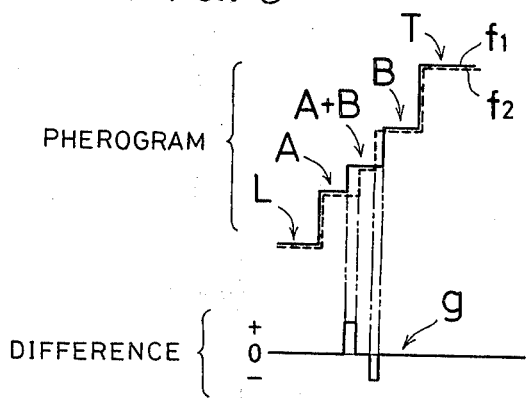
FIG. 5 is a graph explaining the operation of the apparatus shown in FIG. 1.

Generally speaking, the length W (which appears in FIG. 3) from the first step to the final step becomes constant independently of the time, as the time elapses to some extent after the start of the migration, and indicates the total length of the sample zone. On the other hand, the length of the completely separate component zone is also constant independently of the time, as has been described hereinbefore. More specifically, if all the component zones of the sample are completely separated at the position of the detector 7, the pherograms f₁ and f₂ substantially coincide. Therefore, if the positions of the first steps of the two pherograms f₁ and f₂ of FIG. 3, as viewed from the left, are made coincident and if the pherogram f₂ of FIG. 3 is subtracted from the pherogram f₁ of FIG. 3, the remainder becomes zero in the case of the complete separation. If any mixed zone exists at the incomplete separation, on the contrary, it becomes narrower and narrower with the time so that the zones upstream and downstream thereof will accordingly broaden. As a result, the pherograms f₁ and f₂ fail to coincide so that the remainder fails to become zero if the pherogram f₂ is subtracted from the pherogram f₁. In the case of the incomplete separation, more specifically, a positive or negative remainder is obtained by the subtraction to attain such a result as is indicated at g in FIG. 5 (Incidentally, it is found from that result that the zone indicated at A+B in the example of FIG. 6 is incompletely separate.).

Therefore, the operation circuit 9 may locate the mixed zone, as has been described hereinbefore, thereby to judge whether or not all the zones are completely separate by detecting that the mixed zone still exists in the pherogram $f_2$. In an alternative, the operation circuit 9 may calculate the remainder between the two pherograms $f_1$ and $f_2$ to detect whether or not the remainder becomes zero all over the pherogram thereby to judge whether or not all the zones are completely separate. More specifically, the operation circuit 9 may store the data, which are obtained by the two detectors 7 and 8, detect the addresses, in which the rising portions of the first steps of the respective pherograms are stored, proceed the designations one by one from those addresses thereby to read out and subtract of the detected outputs, and judge whether or not the absolute value of the remainder is larger than a predetermined value thereby to further judge it as the incomplete separation of components, in case the remainder is equal to or larger than the predetermined value, to feed the control board 10 with an output indicating the incomplete separation, and as the complete separation, if the remainder fails to exceed the predetermined value, to feed the conrol board 10 with an output of the complete separation.

Figure 6:
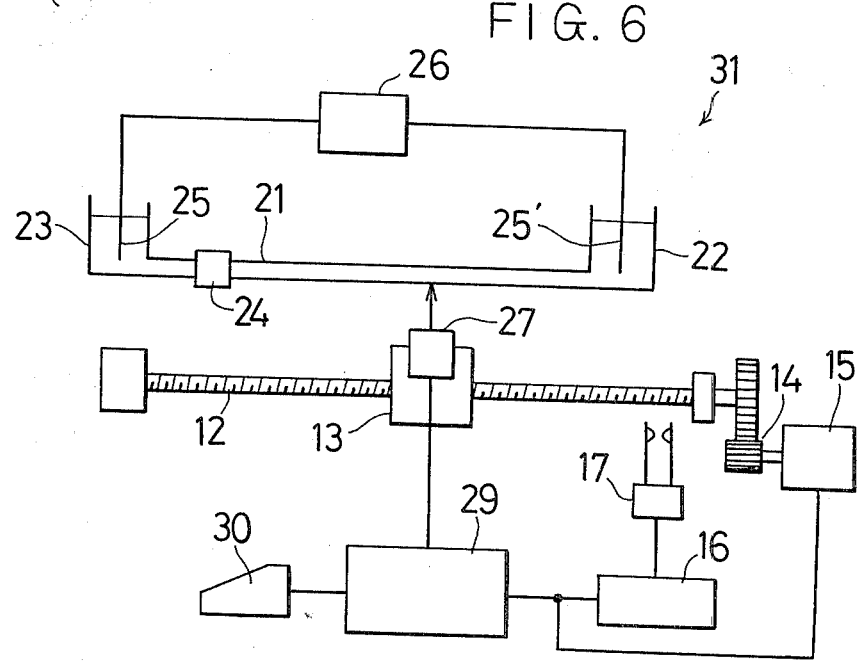
FIG. 6 is a schematic view showing an electrophoretic apparatus according to another embodiment of the present invention.

FIG. 6 shows another embodiment of the present invention. Reference numerals 21, 22 and 23 indicate an electrophoretic tube, a leading electrolyte bath and a terminal electrolyte bath, respectively, and other respective parts are indicated at reference numerals according to those of FIG. 1. The ions to be considered electrically migrate to the right. In the case of this second embodiment, a detector 27 is a thermometer which is carried by a nut 13 screwed on a feed screw 12 arrenged in parallel with the electrophoretic tube 21 so that it can be brought along the electrophoretic tube 21 by turning the feed screw 12 through a gear 14 by means of a pulse motor 15. Since the current to flow in the electrophoretic tube 21 is equal at any section, the zone having a high potential gradient generates much heat so that the potential gradient can be detected by measuring the temperature.

The driving pulses to be impressed from an operation circuit 29 upon the pulse motor 15 are counted by means of a counter 16 so that the position of the detector 27 is expressed by that counted value. The counter 16 is cleared, when the nut 13 is fed to the right to turn on a switch 17, and is rendered operative to count the pulses for driving the motor 15 when the switch 17 is turned off. Specifically, the position of the detector 27, at which the nut 13 abuts against the switch 17, provides an origin for shift measurement.

The operation circuit 29 partly controls the shift of the detector 27, as has been described hereinbefore, and partly samples both the instants when the detector 27 starts its scanning operation and the detected outputs each time the detector shifts a unit distance thereby to store them in a memory.

The shifting speed of the detector 27 is far higher than the electrophoretic migration speed of the ions so that the migration distance during the scanning period can be ignored. Therefore, the records of the detected outputs when the detector 27 is leftwardly shifted from the origin at a certain instant can be deemed to be pherograms, and the starting instant of the scanning operation can be deemed to be that at which those pherograms are prepared. This instant is detected by calculatng the clock pulses, which are oscillated from the operation circuit 29 itself, during the time period from the instant when the operation circuit 29 is started.

If the scanning operation is performed at a certain instant and if the electrophoretic tube 21 is agains scanned at a slightly later instant by means of the detector 27, two pherograms at different instants can be measured and stored. Since the zones at the different instants can be detected from those pherograms, desired data can be attained if the processings similar to those of the electrophoretic apparatus 11 of the foregoing embodiment are conducted.

In the case of the apparatus 31 according to the second embodiment, moreover, since the scanning operations can be repeated, the pherogram at the instant when the sample is completely separated can be obtained if a plurality of pherograms at different instants are measured and stored by performing the scanning operations at predetermined time intervals, if the data stored are read out to calculate the remainder between the two pherograms at adjoining intervals until the remainder can be deemed to be zero all over the pherograms and if the pherogram at the final scanning operation is fed to a recorder so that it may be drawn.

Since the electrophoretic apparatus according to the present invention has the construction thus far described, it is possible to discriminate whether or not each zone of the pherograms is a complete separate one thereby to avoid an error that an incomplete separate zone is judged as a zone containing one component. Moreover, since it is possible to determine from the incomplete separate zone either the length of each component zone after the complete separation, i.e., the quantity of each component or the quantity of the sample, in which the complete separation can be effected at a predetermined migration distance, it is unnecessary to elongate the electrophoretic tube so much so that the migration distance can be shortened. It follows that the voltage of the constant current power supply may be relatively low and that the time period required for the measurement can be shortened. Still moreover, it is possible to easily confirm whether or not the separation of the sample is completed. The effects thus far described are especially prominent in the capillary type isotachophoretic apparatus using a capillary tube to provide an electrophoretic column.

In a modified embodiment, furthermore, means for measuring the conductivity, spectroscopic absorptivity or the like can be naturally used as the detectors 7, 8 and 27.

Since the above as well as other modifications and changes are intended to be within the scope of the present invention, the foregoing description should be construed as illustrative and not in the limiting sense, the scope of the invention being defined by the appended claims.

What is claimed is:

1. An electrophoretic apparatus including a sample introduction system and a measurement system arranged in this order in an electrophoretic column connected between terminal and leading electrolyte bathes which in turn are connected to both the ends of a high voltage power supply circuit, wherein the improvement resides in that said measurement system includes means for detecting zones of respective sample component ions at different instants of time, means for detecting the lengthes of zones detected, and operation means for comparing the lengthes of the two corresponding zones detected at different instants of time thereby to determine that the two zones are completely separate ones when separation of said zones is completed, when their lengthes can be deemed to be equal, but otherwise the same as incompletely separate zones.

2. An electrophoretic apparatus as set forth in claim 1, wherein the means for detecting the zones at different instants has two electrophoretic detectors disposed along an electrophoretic tube at a spacing from each other.

3. An electrophoretic apparatus as set forth in claim 2, wherein the means for detecting the lengthes of the zones is made operative to measure the time interval from the instant when the leading end of a zone is detected by said zone detecting means to the instant when the trailing end of the zone is detected.

4. An electrophoretic apparatus including a sample introduction system and a measurement system arranged in this order in an electrophoretic column connected between terminal and leading electrolyte bathes which in turn are connected to both the ends of a high voltage power supply circuit, wherein the improvement resides in that said measurement system includes means for detecting zones of respective sample component ions at different instants of time, means for detecting the lengthes of zones detected, said means for detecting the zones at different instants and said means for detecting the lengthes of the zones are constructed of a single electrophoretic detector adapted to be moved along an electrophoretic tube, and means for detecting the migration distance of said detector, and operation means for comparing the lengthes of the two corresponding zones detected at different instants of time thereby to determine that the two zones are completely separate ones when separation of said zones is complete, when their lengthes can be deemed to be equal, but otherwise the same as incompletely separate zones.

5. An electrophoretic apparatus as set forth in any of the preceding claims 1 to 4, further including operation means for calculating the lengthes of the component zones, when the incompletely separate zones are completely separated, from the lengthes of the corresponding zones at different instants.

6. An electrophoretic apparatus as set forth in any of the preceding claims 1 to 4, further including operation means for calculating the quantity of a sample, in which the separation of its components can be completed at a predetermined electrophoretic distance, from the lengthes of the corresponding zones at different instants.

7. An electrophoretic apparatus as set forth in any of the preceding claims 1 to 4, further including operation display means for displaying completion of the separation, in case all the zones of the sample are judged as the completely separate ones, and incompletion of the separation in the otherwise case.

8. An electrophoretic apparatus as set forth in any of the preceding claims 1 to 4, wherein said electrophoretic column is made of a capillary tube.

* * * * *